(12) United States Patent
Tanassi et al.

(10) Patent No.: US 6,705,726 B2
(45) Date of Patent: Mar. 16, 2004

(54) INSTRUMENT FOR EYE EXAMINATION AND METHOD

(75) Inventors: Cesare Tanassi, Pont della Priula (IT); Dott. Stefano Piermarocchi, Padua (IT); Philip M. Buscemi, Greensboro, NC (US)

(73) Assignee: Nidek Co., Ltd., Gamagori-Aichi (JP)

(*) Notice: Subject to any disclaimer, the term of this patent is extended or adjusted under 35 U.S.C. 154(b) by 114 days.

(21) Appl. No.: 10/079,683

(22) Filed: Feb. 20, 2002

(65) Prior Publication Data

US 2003/0156258 A1 Aug. 21, 2003

(51) Int. Cl.$^7$ .................................................. A61B 3/14
(52) U.S. Cl. ........................................................ 351/206
(58) Field of Search ................................. 351/200, 205, 351/206, 208, 211, 212, 221, 246, 239, 243

(56) References Cited

U.S. PATENT DOCUMENTS

| | | | |
|---|---|---|---|
| 3,864,030 A | * | 2/1975 | Cornsweet |
| 4,283,124 A | * | 8/1981 | Matsumura |
| 4,400,070 A | * | 8/1983 | Isono et al. |
| 4,511,227 A | * | 4/1985 | Nunokawa et al. |
| 4,673,264 A | * | 6/1987 | Takahashi |
| 4,715,703 A | | 12/1987 | Cornsweet et al. |
| 4,838,679 A | | 6/1989 | Bille |
| 5,054,907 A | * | 10/1991 | Sklar et al. ............... 351/212 |
| 5,252,998 A | | 10/1993 | Reis et al. |
| 5,760,872 A | | 6/1998 | Reis et al. |
| 5,892,569 A | * | 4/1999 | Van de Velde ............. 351/221 |
| 5,943,116 A | * | 8/1999 | Zeimer |
| 6,059,773 A | | 5/2000 | Maloney et al. |
| 6,086,205 A | * | 7/2000 | Svetliza |
| 6,273,565 B1 | | 8/2001 | Matsumoto |
| 6,296,358 B1 | * | 10/2001 | Cornsweet et al. |
| 2002/0052551 A1 | * | 5/2002 | Sinclair et al. |

FOREIGN PATENT DOCUMENTS

| | | |
|---|---|---|
| EP | 1 138 256 A2 | 10/2001 |
| EP | 1 183 992 A2 | 3/2002 |
| JP | 2257928 | 10/1990 |
| JP | 7079914 | 3/1995 |
| WO | PCT/DE89/00643 | 10/1989 |
| WO | WO 01/60241 A1 | 8/2001 |

OTHER PUBLICATIONS

Rodenstock SLO "Scanning Laser Ophthalmoscope" brochure (undated).

Heidelberg Retina Tomograph by Laser Scanning Tomography brochure (undated).

NAVIS Software System Brochures (undated) (Parts A, B, C, D, E and F).

6, 7 ,8, and 9 were all known and commercially available prior to applicants' conception of their invention and should be considered as prior art by the Examiner.

* cited by examiner

*Primary Examiner*—George Manuel

(57) ABSTRACT

The present invention relates to a novel instrument for the examination of an eye, namely the retina. The instrument features a LCD display for projection of various types of patterns and stimuli via an optical system onto the retina. The retina can be visualized by live IR image sequences as well as by visible light still frame images. It combines five examination types within one instrument, namely a perimetry examination, a microperimetry examination, a fixation stability examination, a scotoma boundary detection and psychophysical examinations.

37 Claims, 3 Drawing Sheets

INSTRUMENT FOR EYE EXAMINATION AND METHOD

FIELD OF THE INVENTION

The present invention relates to the field of optical instruments for the examination of eyes. Such instruments are mainly used by medical practitioners and in clinics. The inventions relates mainly but not exclusively, to the examination of the human eye. It further relates mainly but also not exclusively, to the examination of the eye retina.

DESCRIPTION OF THE PRIOR ART AND OBJECTIVES OF THE INVENTION

As prior art the following documents are mentioned: WO 90/03759 shows an optical instrument for examination of an eye using a light beam to scan a part of the retina and to produce images point by point according to a scanning method.

U.S. Pat. No. 4,838,679 shows a scanning optical instrument for the examination of an eye. Therein, a laser is used as light beam to scan a front part of the eye. A photo multiplier and an image memory serve to build up an image.

U.S. Pat. No. 4,715,703 shows an optical instrument for examination of an eye with a light source for illuminating the retina, an optical system for forming images of said retina and an electronic camera for producing data signals of said images. This instrument is not a scanning instrument.

Further, optical instruments using scanning systems are known in the market, such as the scanning laser ophthalmoscope of Rodenstock SLO and the laser scanning tomograph by Heidelberg Engineering.

Various software has been used in the past such as the NAVIS System database for optical instrument control and data recording.

Thus, with the prior art as known above, it is an object of the invention to provide a novel instrument and method for the examination of an eye.

It is another objective of the invention, to provide an optical instrument for the examination of an eye that has an improved flexibility.

It is still another objective to provide an optical instrument and method of the non-scanning type using an electronic camera to produce data signals of images formed in said camera with a light source to produce visible light patterns projected on the region of the eye.

Another objective of the invention is to provide a display as the light source in order to have flexibility in producing various patterns.

Various other objectives and advantages of the present invention will become apparent to those skilled in the art as a more detailed description is set forth below.

SUMMARY OF THE INVENTION

According to one aspect of the invention, it is proposed to use a LCD-display (liquid crystal display) for producing said light patterns. This relates to the optical instrument as well as to a method as described below.

An LCD-display offers very high resolution and is very flexible in view of the selection of the form, number, intensity as well as the movement of patterns and is available as a color display with a large multiplicity of colors for display.

According to a second aspect of the invention, the retina of the eye is examined and the optical instrument as defined herein comprises a computer control system for regulating the optical instrument, an input device to enable a patient to input a reaction during examination and an IR light source for illuminating the retina via the optical system. The electronic camera used is an IR camera which produces live image sequences. The optical instrument is also adapted to perform five different examination types, namely perimetry examinations, microperimetry examinations, fixation stability examinations, scotoma boundary detections, and psychophysical examinations.

During the perimetry and microperimetry examinations, the display produces fixation target patterns for fixation of the patient's eye and light stimuli for stimulation of the patient's eye. Light stimuli are selectable in position and intensity. The input device is used to detect a patient's reaction as the stimuli is seen. By choosing various retinal positions, information concerning the sensitivity of the considered retinal region can be obtained, e.g. a complete sensitivity map.

During a fixation stability examination, eye fixation is performed by means of the above mentioned fixation target pattern. The optical instrument simultaneously performs live imaging of the retina, wherein the computer control system uses a correlation algorithm to detect movements of the retina and to collect fixation position movement data.

During a scotoma boundary detection, the above mentioned light stimuli are moved in their (projected) position on the retina towards a scotoma boundary region. The above mentioned input device is used to detect the patient's reaction on whether a light stimulus, that has been seen before, vanishes or, vice versa, a light stimulus appears that has not been seen before. Thus, the scotoma boundary can be determined.

There also exists a variety of psychophysical examinations that have common test patterns for selection and projection onto the retina which is imaged in live image sequences simultaneously.

According to the second aspect of the invention, the optical instrument is adapted to offer all five examination types within one instrument and thus avoid the necessity of different instrument types and to shorten and ease a detailed examination session.

Preferably, the optical instrument according to the invention comprises an electronic camera for visible light as an additional or as the only electronic camera. The electronic camera for visible light thus provides "natural" images of the eye fundus obtained with visible light. However, in order to avoid a steady illumination of the eye in the visible spectrum, it is preferred to use a flashing light and thus to produce still images. Live sequences can be obtained by the IR system mentioned above.

Further it is preferred to use a mirror aperture in the optical system for reflecting illumination light from the IR light source via front lens into the eye. A central aperture of the mirror can first be used to transmit light from a front lens for an image of the eye region examined both for IR images and for visible light images. Further this aperture can be optically conjugated with the cornea in order to avoid a direct illumination of the cornea and for cornea reflex. The mirror aperture can also be used to couple invisible light from a flashing light via the front lens into the eye as with the IR illumination light.

The flashing light can be coupled into the optical path for the IR illumination light by means of a cold mirror which will reflect visible light and be transparent for IR light.

The visible light for the electronic camera can be branched-off the optical main path by a movable mirror which, preferably, is used to reflect light from the display to a calibration light sensor by means of its back side.

Further it is preferred that the computer control system of the optical instrument includes an autotracking system for automatically tracking fundus movements during the examination. Therein, a correlation algorithm is used for comparing image frames which can be a grey scale correlation algorithm. This algorithm returns the x and y shifts and the rotation of the currently acquired frame with respect to a reference frame. Preferably, the IR image frames of the live image sequences are used. By means of the correlation algorithm, image shifts between subsequent frames can be detected in order to control an adaptation system that automatically adapts the stimuli projection system to the eye fundus shifts. The x and y offsets of the fundus shifts and the value of the fundus rotation are then used to properly locate the stimulus on the LCD display in that position conjugated with the retinal area which the operator wants to stimulate.

The computer control system preferably selects a sub frame in a reference image which contains contrast structures for correlation calculations and the algorithm is performed only with regard to the sub frame. A preferred feature of the optical instrument according to the invention is that the auto tracking function can be used in each of the above mentioned examination types in order to improve speed, stability and quality of the examinations and images provided.

Finally, it is preferred that the computer control system be able to superpose graphical visualizations of examination results on still frame images, e.g. to produce still frame images with detected parts of a scotoma boundary or with sensitivity point measurements and the like.

The above explained embodiments of the invention and features refer both to the optical instrument and to the methods thereof.

DETAILED DESCRIPTION OF THE PREFERRED EMBODIMENTS AND OPERATION OF THE INVENTION

The invention will be further clarified by the following description of a preferred embodiment. However, this embodiment is explained merely for illustrative purposes and not intended to limit the scope of the invention in any way. Features disclosed can also be relevant in other combinations and are meant with respect to both the apparatus and the method.

Figure 1:
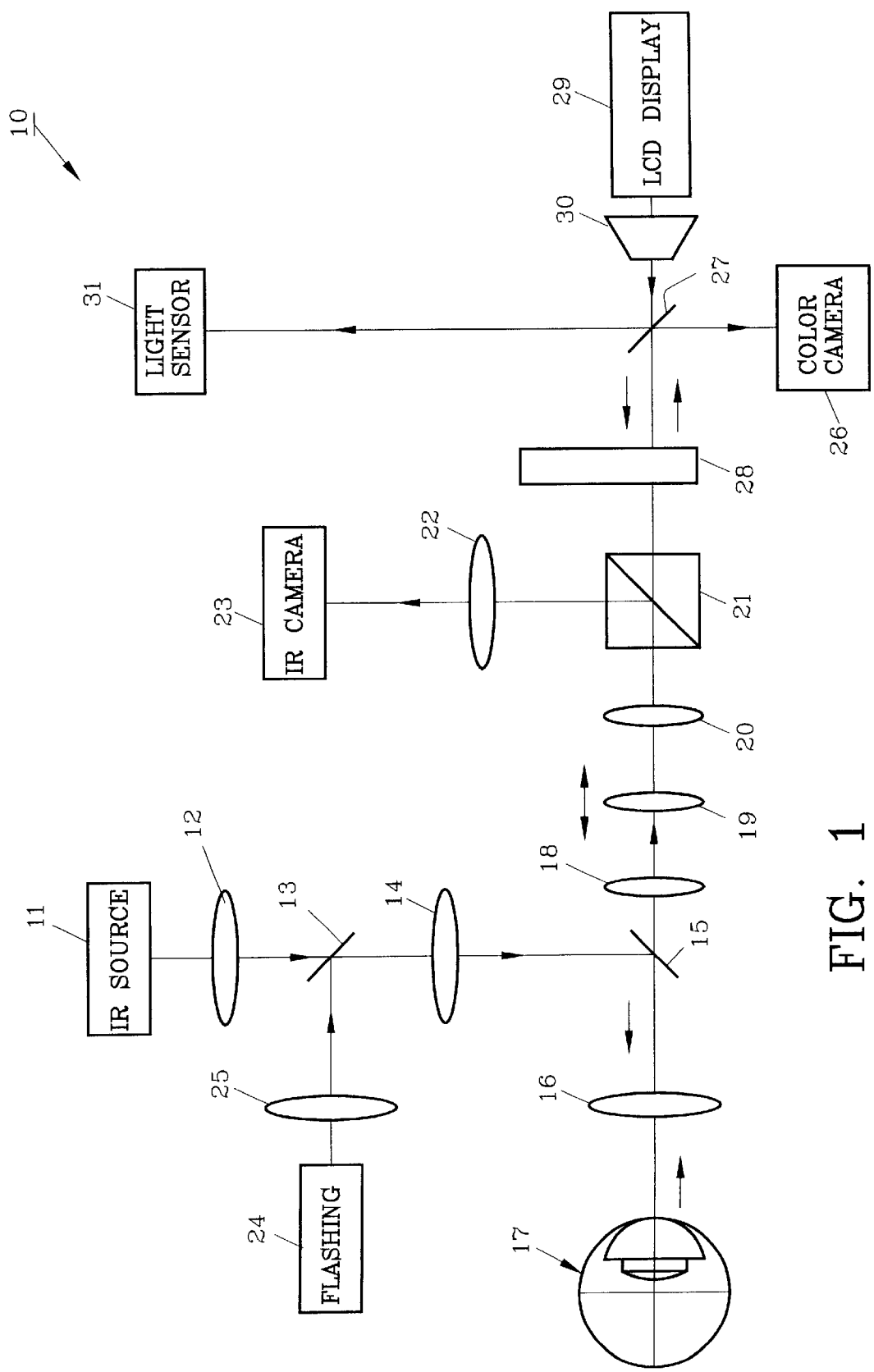
FIG. 1 shows a schematic diagram of an optical instrument for the examination of an eye according to the invention.

FIG. 1 shows a schematic diagram of optical instrument 10 having architecture comprising an IR light source 11 which can be a single IR-LED (infra red light emitting diode) or can even be a cluster of a multiplicity (e.g. 9) IR-LEDs or a halogen lamp with an IR band pass filter. IR light emitted by IR source 11 is directed through condenser lens 12 and transmitted through a cold mirror 13 and a lens group 14. It is reflected by mirror 15 having an aperture in its center. From mirror 15 the IR light passes through a front lens system 16 that can be a single front lens or multiple lenses. From front lens system 16 the IR light is directed into an eye 17 of a patient. Eye 17 is not a part of instrument 10 but is shown for illustrative purposes.

The aperture in mirror 15 is optically conjugated to the cornea of eye 17 and thus avoids an illumination of the cornea by focused light and corneal reflex in the image produced.

As also seen in FIG. 1, the IR light follows an optical side path from IR source 11 to mirror 15 and is coupled into an optical main path to be described later that is horizontal in FIG. 1. A part of the above mentioned optical side path, namely from cold mirror 13 to mirror 15, is also used by visible flashing light emitted from a flashing lamp 24 and transmitted through a condenser lens group 25 onto cold mirror 13. Thus, cold mirror 13 serves to couple the visible flashing light into the optical side path of the IR light.

Front lense 16 forms an image of the retina of eye 17 that is illuminated by IR source 11 and/or flashing lamp 24. This image passes through the aperture in the center of mirror 15 and thus propagates therefrom in the right direction in FIG. 1 through lenses 18, 19 and 20. Again, these lenses can be lens systems according to technical considerations as familiar to those skilled in the art. Lens 19 can be moved in the direction of the optical axis by a commercial stepper motor (not shown) and thus can be used to compensate spherical optical defects of eye 17.

The retina image then passes through a beam splitter 21 that reflects part of the main optical axis through a further lens 22 into IR camera 23. Thus, the optical system of lenses 16, 18, 19, 20 and 22 produces an IR image of the retina in IR camera 23. Since IR camera 23 is an electronic video camera and IR source 11 can be used to continuously illuminate the retina, IR camera 23 can produce continuous data signals representing live image sequences of the retina of eye 17.

The remaining light passing through lenses 18, 19 and 20 is transmitted through beam splitter 21 and also through lens group 28. From lens group 28, the light is directed onto mirror 27 and reflected thereby into color video camera 26. LCD display 29 and the retina as well as the CCD elements of cameras 23 and 26 are optically conjugated. Thus, the optical system of lenses 16, 18, 19, 20 and 28 produce a visible light image in color video camera 26 if flashing lamp 24 is activated. It follows, that color video camera 26 provides still frame images. Mirror 27 is movable (by a solenoid—not shown in the drawing) in order to be removed from the optical main path coming from eye 17 to mirror 27. If removed, the light from lens group 28 will not find camera 26. However, in this situation, LCD display 29 can, via a wide-angle objective 20 to illuminate the retina of eye 17 via the optical main path. LCD display 29 can be used to project arbitrary types of symbols, stimuli and the like of programmable position, color, intensity, and movement onto the retina.

The back side of movable mirror 27, i.e. the side facing upwards to the right in FIG. 1, can be used to reflect light from LCD display 29 into light sensor 31 in order to have an automatic calibration of the intensity at regular intervals.

It is to be understood that mirrors 13, 15 and 27 need not have an angle of 45° to the optical axes but can have arbitrary angles to the optical axes depending on how to best fit into a housing and other considerations.

Lens group 28 is also movable by a stepper motor (not seen) along the optical axis (i.e. horizontally in FIG. 1).

Thereby, an operator can change the field of view of the still frame color images of color video camera 26 between two values, i.e. 15° and 45°. Thus, the operator has the possibility to select the size of the area of the retina to be examined.

Examinations can be done by projecting light patterns of LCD display 29 through lenses 30, 28, 20, 19, 18 and 16 onto the retina of eye 17.

The pattern projected on the retina has a predetermined intensity by means of regular calibrations with light sensor 31 and an automatic software procedure.

IR video camera 23 can monitor the retina during stimulation or testing with stimuli and patterns from LCD display 29. By using the solenoid to insert mirror 27, single still frame images with visible light provided by flashing lamp 24 can be shot between these examinations.

Figure 2:
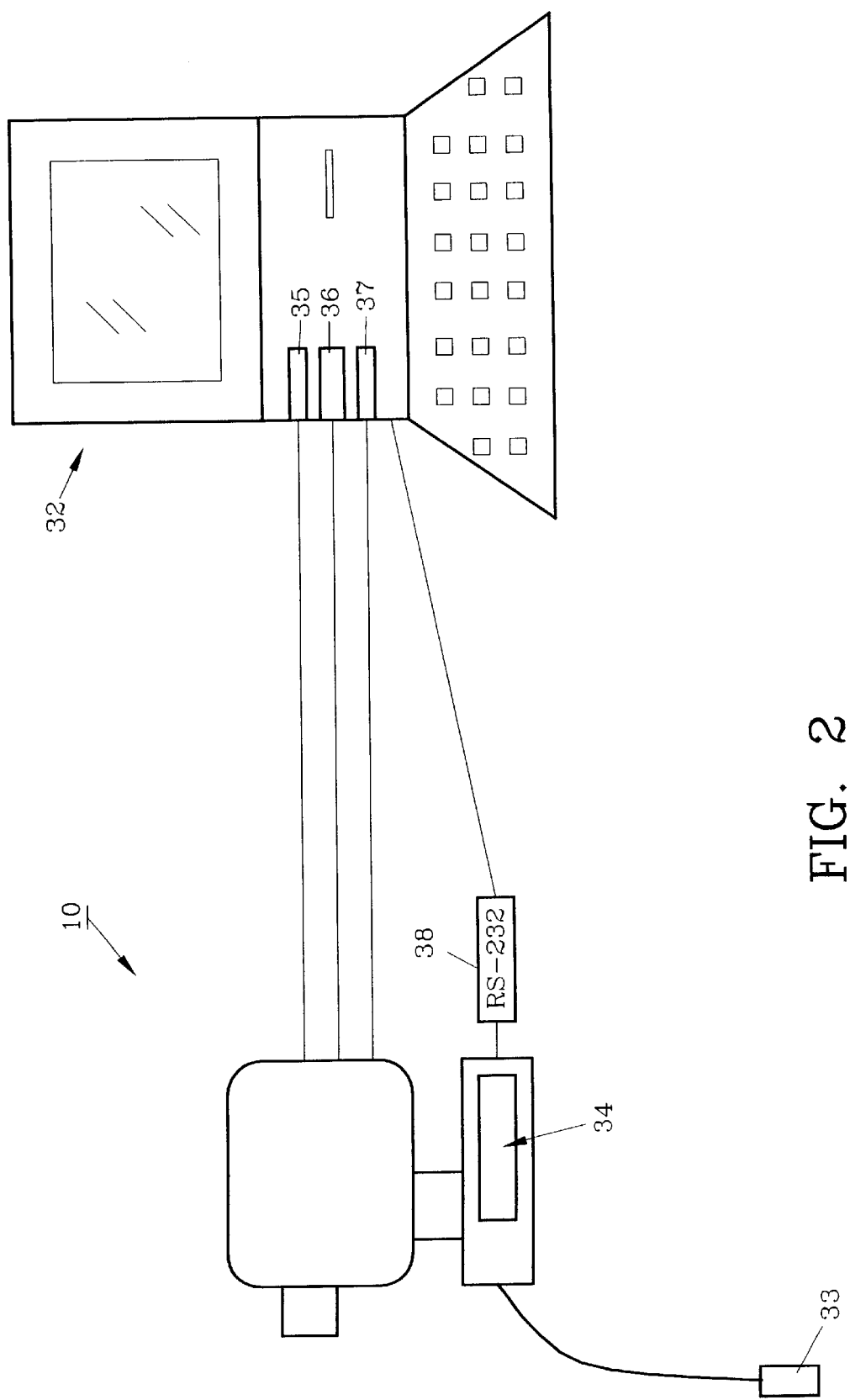
FIG. 2 shows a schematic diagram of the interactions between the optical instrument of FIG. 1 and a computer control system.

Optical instrument 10 is highly automated and therefore connected to a personal computer for control and image collection and processing. FIG. 2 illustrates optical instrument 10 of FIG. 1 on the left side and personal computer 32 on the right side. Further, instrument 10 has an input device 33 which is a hand-held key switch or "trigger".

FIG. 2 shows instrument 10 further comprising an application specific electronic board 34 which is adapted to manage serial communications between instrument 10 and personal computer 32. Electronic board 34 thus is responsible for the movement of mirror 27 (FIG. 1) by the solenoid control of the stepper motors (not seen), moving lenses 19 and 28, operation of IR source 11, of flashing lamp 24, LCD display 29, IR video camera 23, color video camera 26, light sensor 31 as well as connection to input device 33. Also, CCD cameras 23 and 26 provide IR video signals and color image signals to be sent directly to frame grabber 35 in personal computer 32. The display functions of LCD display 29 are controlled via a dual-head video device 36, also seen in personal computer 32. A secondary display output of personal computer's 32 display adapter is used, wherein the software used takes advantage of a set of application programming interfaces (in Windows '98) for the management of secondary displays. Thus, the Windows graphic display interface can be used to fill the display background and project the symbols requested by the operator. Electronic board 34 is connected to communication board 37 of personal computer 32 by means of standard RS-232 interface 38.

For the automatic fundus tracking, personal computer 32 comprises software that uses a normalized grey scale correlation over a 128×128 pixel model between successive frames in order to detect shifts of the patient's fundus. The frames are those from IR video camera 23 and the calculation is performed in real time during the image acquisition. In this embodiment, each time interval between successive frames of 40 ms contains a calculation, i.e. each successive frame is taken into account.

The software chooses the position of the 128×128 pixels subframe in a high contrast part of the IR image. The shifts detected are compensated by a software tool in the image processing within personal computer 32. I.e., optical instrument 10 (as shown in FIG. 1) is not affected.

For perimetry and microperimetry examinations (fundus-related perimetry) light stimuli can be programmed in personal computer 32 to be displayed by LCD display 29 and be projected on the patient's retina on given retina positions. During the examination, the patient's retina is continuously monitored by IR video camera 23 and the patient is asked to look at a fixation target, e.g. a cross, which can also be displayed by LCD display 29. Input key switch 33 can be used by the patient to input whether he can see a stimulus or not.

During the perimetry and microperimetry examinations, the automatic fundus tracking is continuously working in order to stabilize the examination conditions. The operator can therefore see a stable image of the retina and select positions on which light stimuli of varying intensity can be projected in order to detect the sensitivity of the retina. Thus, a sensitivity map or at least a collection of various sensitivity data of a selected retina region is generated.

The stimuli's presentation usually refers to a given shape, a given color and a predetermined amount of time (e.g. 200 ms). The medical details of such examination are known as such and need not be repeated in detail.

A second examination type checks the fixation stability. Again, the patient is asked to look at the fixation target projected on LCD display 29. For a given period of time, the auto tracking system collects the shift data for compensation of the fundus movements by the automatic fundus tracking system so that personal computer 32 can provide a map of these movements during the examination.

Further, the absolute/relative scotoma area on the patient's retina can be determined by projecting moving light stimuli onto the patient's retina. Usually they move radially starting from the scotoma center in various directions with an operator-specified speed until the patent inputs via input key switch 33 that he can see the stimulus. Thus, the scotoma boundary can be determined. Also during this examination, the autotracking system works continuously to stabilize the examination conditions. At the end of the examination a scotoma boundary map can be generated and superposed on a still frame image.

Finally, various known psychophysical tests can be performed by projecting different patterns as e.g., the Amsler grid onto the retina and imaging as well as tracking the patient's fundus.

Figure 3:
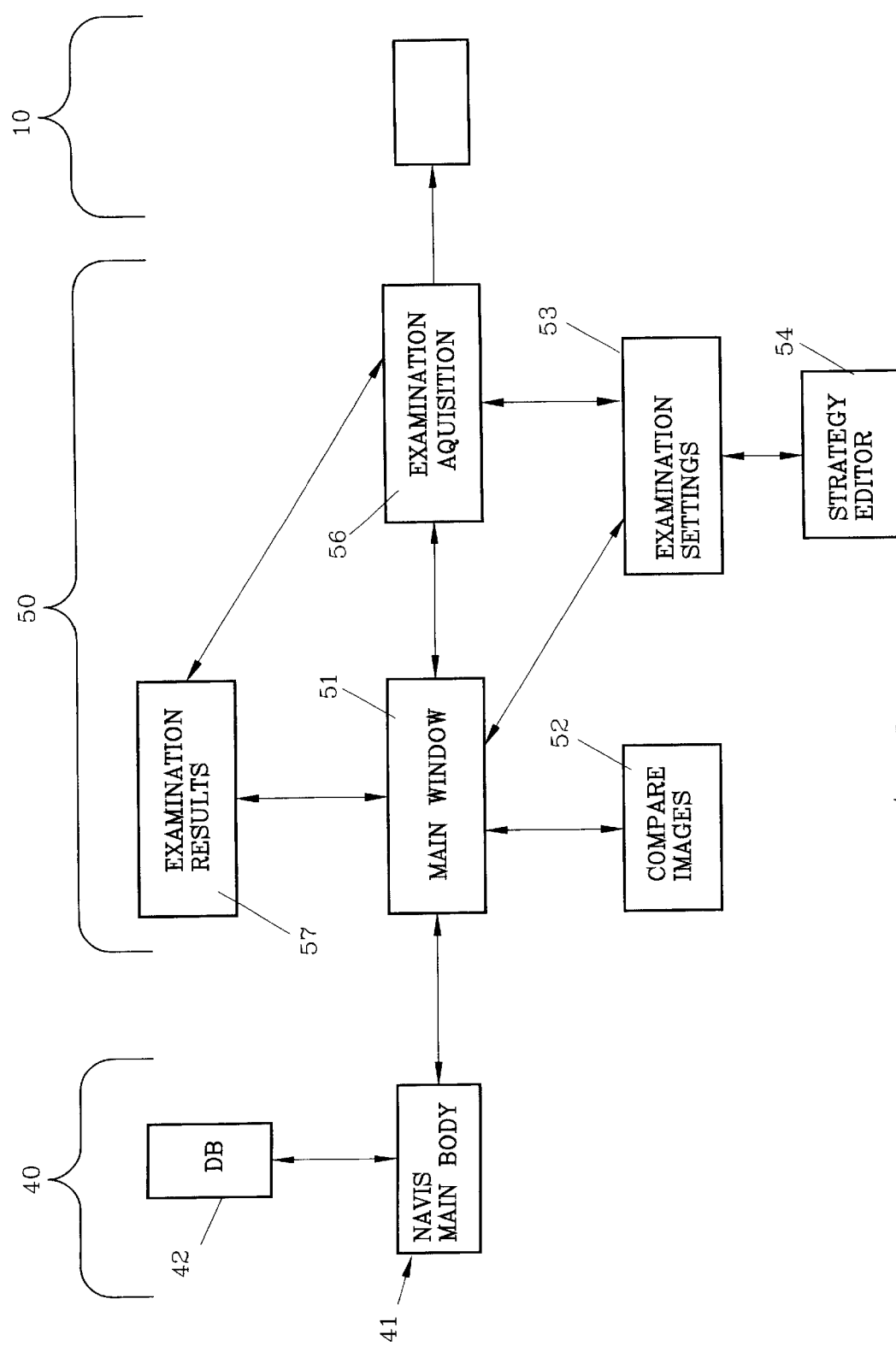
FIG. 3 shows a schematic diagram of the software architecture for explaining the function of the computer control system of FIG. 2.

The software running in personal computer 32 is schematically shown in FIG. 3. It is based on the NAVIS system 40 (Nidek Advanced Vision Information System) which is a basic data base and application software 50 running in the background in personal computer 32.

NAVIS system 40 has a main body 41 and database 42 connected to dedicated application software 50 that communicates with database 42 via main body as seen in FIG. 3. The interface between application software 50 and main body 40 is a dynamically linked library (not shown) allowing interprocess communication through allocation of file mapped memory space.

Application software 50 comprises several blocks, the central one of which communicates with the main body 40 as main window 51. This is the entry window from which it is possible to access all other windows and on which the current patient's visit and examination are displayed. Further this main window 51 displays all images available for the current examination and image information related thereto.

The examination results window 57 is accessible from main window 51. Window 57 includes a set of windows for the qualitative and quantitative results to be displayed and printed by a printing tool of the software. The result windows are individual for the five different examination types previously described.

From the main window and also from examination result windows 55, examination acquisition window 56 can be accessed to, and is used for the definition of the interactions between optical instrument 10 and personal computer 32 by the operator.

From main window 51, compare images window 52 can be chosen to obtain comparative views between images and examinations acquired at different times.

A further choice staring from main window 51 is examination settings window 53 for configuring the examination modalities. The pattern and stimulus projection strategy and type, the fixation target and the background and number of directions of a scotoma boundary detection movement can be chosen. All settings can be saved in a configuration file in order to retrieve them as needed from an archive.

From examination settings window 53, a strategy editor window 54 can be chosen that allows the creation and edition as well as storage of pattern and stimulus projection strategies by the operator.

In these pattern and stimulus projection strategies, the projection details are completely customizable. This is due to the flexibility of the LCD projection. E.g., the following fixation symbols could be used: crosses or circles of given size and color and arrangements of such crosses in given distances, further user-defined symbols or bitmaps. Further, standard Goldman mires of given color or other user defined mires. The background can also be user-defined or monochromatic. The positions and intensities of such stimuli can be stored as a strategy and used during fully automated perimetry and microperimetry examinations without further operator interaction (only with patient response using key switch 33).

The illustrations and examples provided herein are for explanatory purposes and are not intended to limit the scope of the appended claims.

We claim:

1. An optical instrument for examination of an eye comprising:
    a) a light source for producing visible light patterns to be projected on a region of said eye to be examined,
    b) an optical system for projecting said light patterns on said region, for illuminating said region, and for producing images of said region, and
    c) an electronic camera for producing data signals of said images of said region,
    wherein
    said light source comprises a LCD display arranged to produce said light patterns, and said optical system is arranged to project the light patterns produced by the LCD display from the LCD display to the region of said eye to be examined.

2. An optical instrument according to claim 1 wherein said region is a part of the retina of said eye.

3. An optical instrument according to claim 1 comprising an IR light source for illuminating said region of said eye via said optical system and an IR-camera for producing data signals of live image sequences produced in said IR camera by said optical system as well as an electronic camera for visible light.

4. An optical instrument according to claim 1 comprising an IR light source for illuminating said region of said eye via said optical system and an IR camera for producing data signals of live image sequences produced in said IR camera by said optical system and wherein said optical system comprises a mirror for reflecting IR illumination light of said IR light source to a front lens of said instrument being directed to the eye to be examined, said mirror defining a central aperture for light from said front lens for an image of said eye region to traverse said mirror without being reflected.

5. An optical instrument according to claim 4 wherein said aperture in said mirror is optically conjugated with the cornea of said eye to be examined.

6. An optical instrument according to claim 4, further comprising a flashing lamp for producing visible flashing light and a cold mirror for coupling said flashing light into an optical path used for said illumination by said IR light source, going to said apertured mirror.

7. An optical instrument according to claim 1 comprising an IR light source for illuminating said region of said eye via said optical system and an IR camera for producing data signals of live image sequences produced in said IR camera by said optical system and wherein said optical system comprises a beam splitter for branching-off an optical side path for said IR-camera from an optical main path for said display.

8. An optical instrument according to claim 1 wherein said optical system comprises a movable mirror for branching-off an optical side path for an electronic camera for visible light.

9. An optical instrument according to claim 8 further comprising a light sensor for calibration of said display, said movable mirror being adapted to reflect light from said display to said light sensor for calibration of said display.

10. An optical instrument according to claim 1 further comprising a computer control system, said computer control system including an autotracking system using a grey scale correlation algorithm for comparing image frames of said electronic camera with respect to a reference frame and detecting image x and y shifts and rotations therein, said computer control system comprising an adaption system for adapting to said image x and y shifts and rotations.

11. An optical instrument according to claim 10 wherein said adaption system can be used to properly locate stimuli on said LCD display in a position conjugated with a retinal area to be stimulated, by using said x and y shifts and rotations of said eye region.

12. An optical instrument according to claim 11 wherein said autotracking system is adapted to perform said grey scale correlation algorithm only in a subframe of said image frames.

13. An optical instrument according to claim 1 further comprising a computer control system, wherein said computer control system is adapted to superpose a graphical visualization of examination results on still frame images.

14. An optical instrument for examination of an eye retina comprising:
    a) a light source for producing visible light patterns to be projected on said retina,
    b) an optical system for projecting said light patterns on said retina and for producing images of said retina,
    c) an electronic camera for producing data signals of said images of said retina, and
    d) a computer control system,
    wherein said light source is a display being adapted to produce a variety of different patterns of selectable intensity, selectable position and selectable structure,
    that said instrument includes an input device whereby a patient can input a reaction during examination, that said instrument includes an IR light source for illuminating said retina via said optical system and that said electronic camera is an IR camera for producing data signals of live image sequences produced in said IR camera by said optical system, and that said instrument is adapted to perform, within one instrument:

i) a perimetry examination in which said display is need to produce a fixation target pattern for eye fixation and light stimuli of fixed but selectable position and selectable intensity for stimulation of the eye, both to be projected on said retina, wherein said input device is used to detect a patient reaction if said patient can see said stimuli;

ii) a microperimetry examination in which said display is used to produce a fixation target pattern for eye fixation and light stimuli of fixed but selectable position and selectable intensity for stimulation of the eye, both to be projected on said retina, wherein said input device is used to detect a patient reaction if said patient can see said stimuli;

iii) a fixation stability examination in which said display is used to produce a fixation target pattern for eye fixation to be projected on said retina, wherein simultaneously said retina is imaged by said live image sequences, wherein said computer control system uses a correlation algorithm to collect fixation position movement data;

iv) a scotoma boundary detection, wherein said display is used to produce moving light stimuli to be projected on said retina, said projected stimuli moving towards a scotoma boundary on said retina, and wherein said input device is used to detect a patient reaction responsive on whether the patient can see said stimuli;

v) or psychophysical examinations wherein said display is used to produce a psychophysical test pattern selectable from a variety of psychophysical test patterns, to be projected on said retina, and wherein said retina is imaged by said live image sequences simultaneously.

15. An optical instrument according to claim 14 wherein said display is a LCD-display.

16. An optical instrument according to claim 15 wherein said optical system comprises a beam splitter for branching-off an optical side path for said IR-camera from an optical main path for said display.

17. An optical instrument according to claim 15 wherein said optical system comprises a movable mirror for branching-off an optical side path for an electronic camera for visible light.

18. An optical instrument according to claim 17 further comprising a light sensor for calibration of said display, said movable mirror being adapted to reflect light from said display to said light sensor for calibration of said display.

19. An optical instrument according to claim 15 wherein said computer control system includes an autotracking system using a grey scale correlation algorithm for comparing image frames of said electronic camera with respect to a reference frame and detecting image x and y shifts and rotations therein, wherein said computer control system comprises an adaption system for adapting to said image x and y shifts and rotations.

20. An optical instrument according to claim 19 wherein said adaption system can be used to properly locate stimuli on said LCD display in a position conjugated with a retinal area to be stimulated, by using said x and y shifts and rotations of said eye region.

21. An optical instrument according to claim 19 wherein said autotracking system is adapted to perform said grey scale correlation algorithm only in a subframe of said image frames and to let a user select said subframe.

22. An optical instrument according to claim 21 wherein said autotracking function can be used in each of said perimetry, microperimetry, fixation stability, scotoma boundary detection, and psychophysical examinations of claim 14.

23. An optical instrument according to claim 15 wherein said computer control system is adapted to superpose a graphical visualization of examination results on still frame images.

24. An optical instrument according to claim 14 further comprising an electronic camera for visible light.

25. An optical instrument according to claim 14 wherein said optical system comprises a mirror for reflecting IR illumination light of said IR light source to a front lens of said instrument being directed to the eye to be examined, said mirror defining a central aperture for light from said front lens for an image of said eye region to traverse said mirror without being reflected.

26. An optical instrument according to claim 25 wherein said aperture in said mirror is optically conjugated with the cornea of said eye to be examined.

27. An optical instrument according to claim 25 further comprising a flashing lamp for producing visible flashing light and a cold mirror for coupling said flashing light into an optical path used for said illumination by said IR light source, going to said apertured mirror.

28. A method of examining an eye comprising the steps of:
a) producing visible light patterns by means of an LCD display,
b) projecting said light patterns from said LCP display to a region of said eye to be examined by means of an optical system,
c) illuminating said region and producing images of said region by means of said optical system, and
d) producing data signals of said images of said region by means of an electronic camera.

29. A method according to claim 28 wherein a grey scale correlation algorithm in an autotracking system of a computer control system is used for comparing image frames of said electronic camera and detecting image shifts therein and an adaption system of said computer control system is used for adapting to said image shifts.

30. A method according to claim 29 wherein said grey scale correlation algorithm is used only in a subframe of said image frames.

31. A method according to claim 28 wherein a computer control system is used to superpose a graphical visualization of examination results on still frame images.

32. A method of examining an eye retina comprising the steps of:
a) producing visible light patterns by means of a light source,
b) projecting said light patterns on said retina of said eye to be examined by means of an optical system,
c) illuminating said region and producing images of said retina by means of said optical system, and
d) producing data signals of said images of said retina by means of an electronic camera,
wherein said light patterns are produced by means of a display of said light source, said display being adapted to produce a variety of different patterns of selectable intensity, selectable position and selectable structure, and wherein an IR light source is used for illuminating said retina via said optical system and said electronic camera is an IR camera and produces data signals of live image sequences produced in said IR camera by said optical system, and wherein an operator can select, using one and the same optical instrument, between the examination types of:

i) a perimetry examination in which said display is used to produce a fixation target pattern for eye fixation and light stimuli of fixed by selectable position and selectable intensity for stimulation of the eye, both to be projected on said retina, wherein an input device is used to detect a patient reaction if said patient can see said stimuli;

ii) a microperimetry examination in which said display is used to produce a fixation target pattern for eye fixation and light stimuli of fixed by selectable position and selectable intensity for stimulation of the eye, both to be projected on said retina, wherein an input device is used to detect a patient reaction if said patient can see said stimuli;

iii) a fixation stability examination in which said display is used to produce a fixation target pattern for eye fixation to be projected on said retina, wherein simultaneously said retina is imaged by said live image sequences, wherein a computer control system uses a correlation algorithm to collect fixation position movement data;

iv) a scotoma boundary detection, wherein said display is used to produce moving light stimuli to be projected on said retina, said projected stimuli moving towards a scotoma boundary on said retina, and wherein said input device is used to detect a patient reaction responsive on whether the patient can see said stimuli;

v) or psychophysical examinations wherein said display is used to produce a psychophysical test pattern selectable from a variety of psychophysical test patterns, to be projected on said retina, and wherein said retina is imaged by said live image sequences simultaneously.

33. A method according to claim 32 wherein a grey scale correlation algorithm in an autotracking system of said computer control system is used for comparing image frames of said electronic camera with a respect to a reference frame and detecting image x and y shifts and rotations therein, and an adaption system of said computer control system is used for adapting to said image x and y shifts and rotations.

34. A method according to claim 33 wherein said adaption system is used to properly locate stimuli on said LCD display in a position conjugated with a retinal area to be stimulated, by using said x and y shifts and rotations of said eye region.

35. A method according to claim 33 wherein said grey scale correlation algorithm is used only in a subframe of said image frames.

36. A method according to claim 33 wherein said autotracking function can be used in each of said perimetry, microperimetry, fixation stability, scotoma boundary detection and psychophysical examinations.

37. A method according to claim 32 wherein said computer control system is used to superpose a graphical visualization of examination results on still frame images.

* * * * *